United States Patent
Hughes

(10) Patent No.: US 7,469,423 B2
(45) Date of Patent: Dec. 30, 2008

(54) SPRAY-SPECS: A "PINCH OFF" LENS PROTECTION SYSTEM, ITS METHOD OF ATTACHMENT AND REMOVAL, FOR SAFETY GLASSES

(76) Inventor: Scott Lafayette Hughes, 1372 White Dr., Santa Clara, CA (US) 95051

( * ) Notice: Subject to any disclaimer, the term of this patent is extended or adjusted under 35 U.S.C. 154(b) by 0 days.

(21) Appl. No.: 11/047,930

(22) Filed: Feb. 1, 2005

(65) Prior Publication Data

US 2005/0166304 A1    Aug. 4, 2005

Related U.S. Application Data

(60) Provisional application No. 60/540,976, filed on Feb. 2, 2004.

(51) Int. Cl.
*A61F 9/00*    (2006.01)
(52) U.S. Cl. ............................................. 2/15; 2/448
(58) Field of Classification Search .................. 2/15, 2/434, 448; 359/642
See application file for complete search history.

(56) References Cited

U.S. PATENT DOCUMENTS

| | | | | |
|---|---|---|---|---|
| 4,076,373 A | * | 2/1978 | Moretti | 359/507 |
| 4,138,746 A | * | 2/1979 | Bergmann | 2/424 |
| 4,317,240 A | * | 3/1982 | Angerman et al. | 2/436 |
| 4,455,689 A | * | 6/1984 | Boyer | 2/434 |
| 4,563,065 A | | 1/1986 | Kreissl | |
| 4,686,712 A | * | 8/1987 | Spiva | 2/10 |
| 4,716,601 A | * | 1/1988 | McNeal | 2/434 |
| 5,018,223 A | * | 5/1991 | Dawson et al. | 2/436 |
| 5,592,698 A | * | 1/1997 | Woods | 2/424 |
| 5,661,535 A | * | 8/1997 | Wang | 351/120 |
| 5,671,483 A | * | 9/1997 | Reuber | 2/424 |
| 5,809,580 A | * | 9/1998 | Arnette | 2/426 |
| 6,085,358 A | * | 7/2000 | Cogan | 2/424 |
| 6,234,627 B1 | * | 5/2001 | Agnoli | 351/47 |
| 6,241,352 B1 | | 6/2001 | Metcalfe | |
| 6,536,045 B1 | * | 3/2003 | Wilson et al. | 2/15 |
| 6,725,467 B2 | * | 4/2004 | Harding | 2/435 |
| 6,847,492 B2 | * | 1/2005 | Wilson et al. | 359/642 |
| 6,870,686 B2 | * | 3/2005 | Wilson et al. | 359/642 |
| 7,003,811 B2 | * | 2/2006 | Canavan | 2/448 |

* cited by examiner

*Primary Examiner*—Katherine Moran
(74) *Attorney, Agent, or Firm*—Invent Capture, LLC.; Samuel S. Cho

(57) ABSTRACT

A multi layered lens protection system applied to protective eyewear is disclosed. Wherein safety glasses have been made receptive to a plurality of transparent lens protectors by means of two extruding posts located on the front of the main lens and the dimensionally corresponding, specifically designed notches located on the protector. As the outermost protector becomes soiled, a simple pinching motion exerted upon the entire protector, releases it from the posts, revealing another clean protector and thereby restoring a clear view. Whereby the design of the lens protectors, which eliminates the presences of tabs or extensions, facilitates and dictates this pinching motion and in turn provides a most precise and efficient manner of grasping each outermost or soiled protector in order to achieve rapid vision restoration and therefore continuous eye protection.

19 Claims, 8 Drawing Sheets

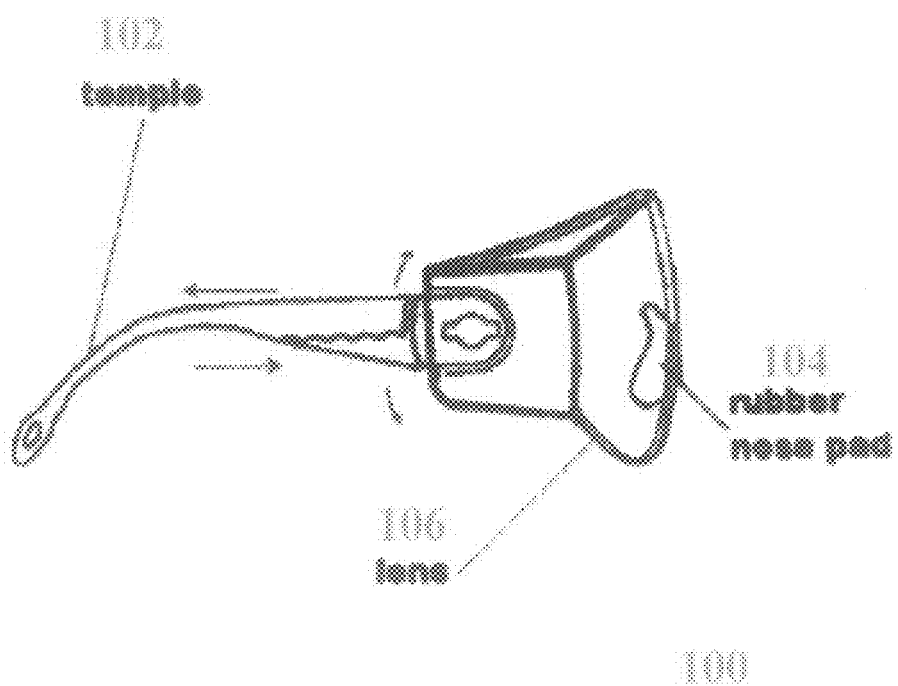

hole and subsequent post locations

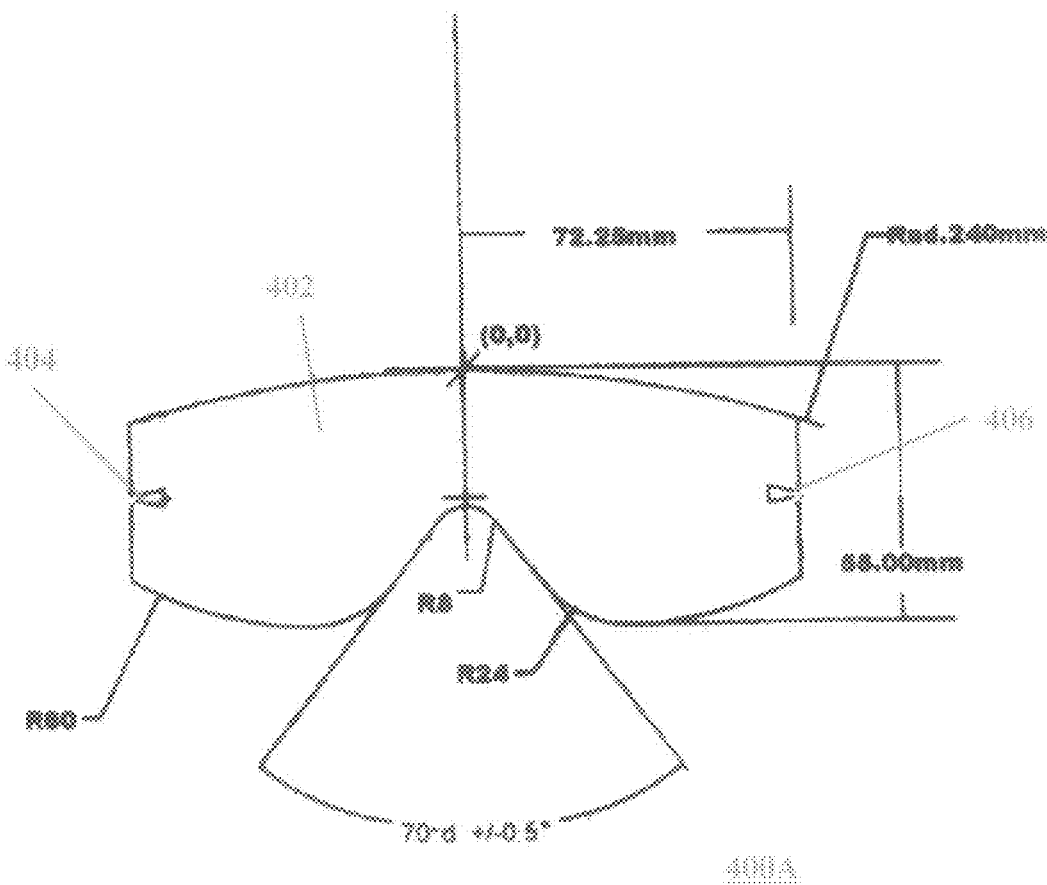

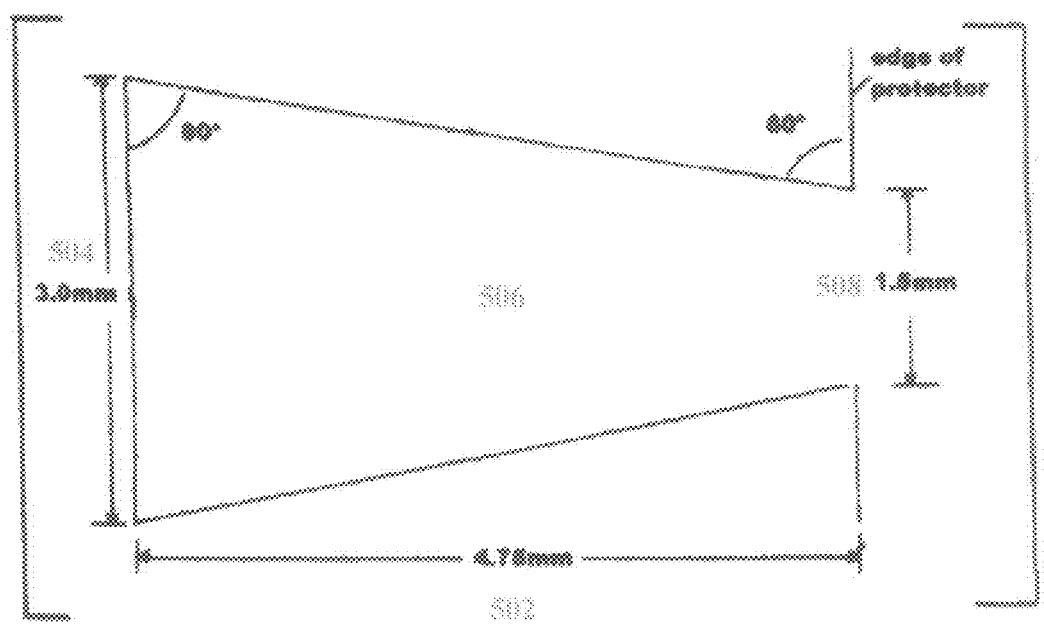

Attach lens protector(s) to posts on main lens via corresponding notches at edge of protector; using either angle shown above to secure notches on posts.

To remove or release each outermost, soiled
protector, simply apply a pinching motion to slide
or dislodge the detailed edges of protector off their posts.

SPRAY-SPECS: A "PINCH OFF" LENS PROTECTION SYSTEM, ITS METHOD OF ATTACHMENT AND REMOVAL, FOR SAFETY GLASSES

CROSS REFERENCE TO RELATED APPLICATIONS (Not Applicable)

STATEMENT REGARDING FEDERALLY SPONSORED RESEARCH OR DEVELOPMENT (Not Applicable)

REFERENCE TO SEQUENCE LISTING, A TABLE, OR A COMPUTERPROGRAM LISTING COMPACT DISC APPENDIX (Not Applicable)

BACKGROUND OF THE INVENTION

This present invention relates to protective eyewear in the form of spectacles or glasses (having temples), which are readily receptive to multiple layers of clear transparent lens protectors, and more particularly, pertains to a method by which said lens protectors are held in place atop the main lens and subsequently removed.

Within many industries, such as the painting, drywall, and pest control, for example, workers are constantly subjected to constant fall-out or bounce-back of light weight particle of materials (ie. over-spray); or may just simply be down wind. Whether spraying paint, drywall texture or chemicals there is not only a need to protect the eyes, but furthermore the need to do so in a manner that allows for convenient, rapid vision restoration.

Having been a painting contractor myself, I have concluded that the industry has been resigned to suffer as a whole, in that there is inadequate eye protection available. Ordinary safety glasses quickly become covered in the paint or chemical being used, thereby decreasing vision. Any attempt to clean the main lens for continuous use is not only timely but often proves futile, in that the paint or chemical can quickly dry to or melt the main lens. Traditional protective eyewear is abandoned. Many workers are resigned to using no eye protection when doing such jobs, often resorting to the minimal protection of a billed cap.

Eye protection devices receptive to or containing multiple layer systems of protectors have been granted patents for the need to address many similar scenarios. Such as moto-sport racing or paint ball, as well as painting. As disclosed in such patents as U.S. Pat. Nos. 4,455,689, 4,716,601 and 5,592,698, these tear off lens (protection) systems incorporate the use of or on a goggle or helmet face shield. As well as discuss their attempts to rectify previous methods of attaching and releasing a plurality of transparent protectors, and the apparatus used to do so. However, inherent in these and many other prior works related to this invention is the presence of a tab or pulling device on the edge of each protector in order to facilitate its release. Despite the different means by which the protectors are held in place atop the main lens; whether it being a extruding post, or an adhesive (U.S. Pat. No. 6,536, 045), and despite any differing attempts in positioning these tabs in prior art, an inherent drawback in these type of protectors [with tabs] is ones ability [while performing a task,] to simply grasp each successive tab in order to pull off the outermost transparent protector in a rapid, efficient, and precise manner.

This rationally used method of protector removal, consisting of a pulling or tearing motion, requires an outwardly (away from head) force being applied to the goggle and thereby necessitates the need for a strap or band to hold the goggles in place on the user's head; so as not to pull off the entire goggle, or the wearing of a large cumbersome helmet. Both are not very conducive to a hobby or working environment. Headbands or elastic straps can be very uncomfortable, as well as having to wear a helmet while working in order to achieve this means of vision restoration; and also regarded as a drawback in these previous works.

U.S. Pat. No. 4,563,065 adapted a lens protection system to glasses or spectacles, but have done so in a manner that requires the presence of "pulling" tabs in order to remove a protector; again thereby necessitating the presence of a head band or strap, and inherently the problematic, precise grasping of the tabs themselves. This invention clearly discusses and attempts to address the need to improve the overall efficiency of grasping an individual tab of the outermost protector.

Yet, within other versions of vision clearing devices, as discussed in U.S. Pat. Nos. 4,528,701 and 5,203,035, rather than a stack of protectors which are to be individually torn away or off, they utilize a long continuous thin layer of film that is to be scrolled across the main lens,-from its holding to its receiving spool or magazine,-as needed to restore a clear view; by manual yet slightly differing mechanical means. Regardless, not only do the presence of receiving or holding spools or magazines on the side of the device negate much peripheral vision, but an added drawback to both is the large, cumbersome, front heavy, nature of these versions making them awkward to use in a construction or painter's environment or in general, and thusly requiring a(n elastic) strap or band to hold on users head. Another drawback found in the latter (U.S. Pat. No. 5,203,035), despite its attempt to house the spools in a die cut paper card, becomes the accumulation of material or debris (paint for example) that builds up on the spooling mechanism; increasingly debilitating its ability to function, or scroll smoothly at all.

Accordingly, there is a need for a more efficient, reliable, lightweight and comfortable version of protective eyewear, that is not only receptive to multiple layers of lens protectors but whose design and make-up is more conducive to consistent performance in the construction or trade industries as well; specifically painting. As well as a need for a method of protector removal or vision restoration that does not require the presence of any tabs or pulling devices on the protectors, nor the need for any adhesives or any added moveable structures or spooling mechanisms that can all therefore dictate the need for a head band or strap (to be worn in order to hold the protective device on the user's head, due to the inherent outwardly force needed to remove a transparent lens protector utilizing the pulling or tearing of said tab, or as a result of the mere presence and added weight of any spooling mechanisms); nor for use upon a goggle or helmet. But rather, one in which the make-up and method of lens protector removal provides an overall improvement to the concept of vision restoration applied to safety glasses.

SUMMARY OF THE INVENTION

The present invention comprises an improvement to a multi-layer safety spectacles. as a protective eyewear for tasks such as spraying paint or chemicals. The present invention utilizes lightweight and stylish safety spectacles each of which places a plurality of transparent layers as lens protectors. Each transparent layer can be removed one at a time as the outermost transparent layer as a lens protector becomes soiled simply by exerting a pinching motion on the surface of the outermost or exposed transparent layer which is used as a lens protector.

In addition, one aspect of this invention is using two dually adjustable temples attached to the multi-layer safety spectacles, wherein each dually adjustable temple is configured to adjust the angle of the the temple relative to the main lens and the temple length.

Furthermore. the multi-layer safety spectacles incorporate two protruding posts located at the opposite edges on the front of the main lens, wherein each protruding post (e.g. 300 of FIG. 3 and 608 of FIG. 6) is configured to hold lens protectors (i.e. transparent layers of film) securely in front of the main lens as shown in FIG. 6.

Another feature present in this invention is a novel notch design of the lens protectors, wherein the novel notch design characterized by a wider to narrow passage as shown in notches 404 and 406 of FIG. 4A and FIG. 5 allows the lens protectors to be held securely in place.

In addition. another feature of the present invention is that the novel notch design of the lens protectors obsoletes a need for grasping a tab or other pulling devices from an edge of the lens protector in order to remove the lens protector from the multi-layer safety spectacles, because the novel notch design of the lens protectors as shown in notches 404 and 406 of FIG. 4A and FIG. 5 enables a unique "pinch-off" method of removing the lens protector without using tabs or other pulling devices.

By using the novel notch design of the lens protectors specifically featured in this invention, a unique "pinch-off" method of removal is enabled. The surface of the outermost lens protector, which is attached to the multi-layer safety spectacles by inserting each notch to corresponding protruding posts (e.g. 300 of FIG. 3 and 608 of FIG. 6) can be "pinched-off" or grasped to remove the outermost lens protector from the multi-layer safety spectacles.

It is important to note that the multi-layer safety spectacles disclosed in the present invention does not necessitate tabs or pulling device unlike conventional safety spectacles, because the removal of each lens protector (i.e typically a transparent layer) is accomplished by simply applying a pinching motion to the outermost lens protector. Because a cinching motion on the surface of a lens protector involves applying an inward pressure toward a user's face, the pinching motion eliminates the need for using a head band or strap in order to keep the multi-layer safety spectacles on user's head while attempting to restore vision by removing a soiled lens protector from the multi-layer safety spectacles.

In summary. the present invention discloses an improved and novel multi-layered safety spectacles with a plurality of transparent lens protectors, wherein the improved and novel multi-layered safety spectacles utilizes unique notch designs to enable a "pinch-off" removal of a soiled protector and eliminate the need for using tabs or pulling devices for removing a lens protector, thereby also eliminating the inherent need for using headband or strap in conventional multi-layered safety spectacles.

These and other advantages and features of the invention and some embodiments of the invention will become more apparent upon viewing and considering the following drawings and detailed description.

DESCRIPTION OF THE SEVERAL VIEWS OF THE DRAWINGS

FIG. 1 shows a side view of multi-layered safety spectacles in accordance with an embodiment of the invention.

FIG. 4A shows a frontal view of a transparent lens protector configured to be placed on top of the main lens, with outlining dimensions defining its shape in accordance with an embodiment of the present invention.

FIG. 5 shows a zoomed-in view of the notch from the transparent lens protector of FIG 4B, wherein the notch is configured to fit a protruding post from the main lens and accommodate a unique "pinch-off" removal of the transparent lens protector in accordance with an embodiment of the present invention.

DETAILED DESCRIPTION OF THE INVENTION

Figure 2A:
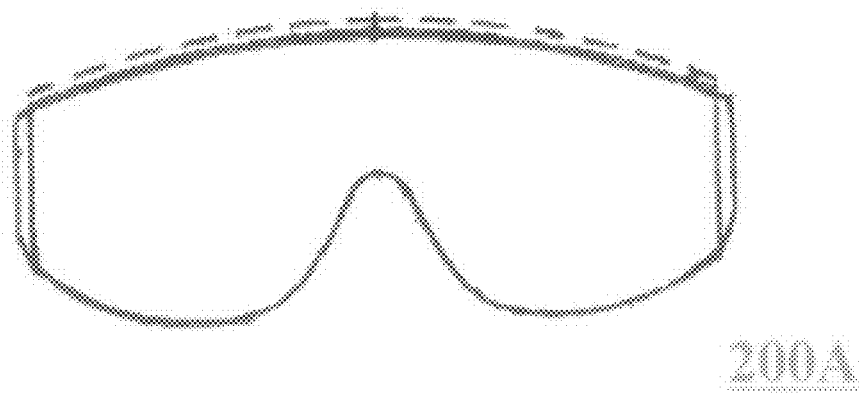
FIG. 2A shows a frontal view of multi-layered safety spectacles in accordance with an embodiment of the present invention.

Specific embodiments of the invention will now be described in detail with reference to the accompanying figures. Like elements in the various figures are denoted by like reference numerals for consistency. In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description. The present invention, commercially named "Spray-Specs." by the inventor, will now be further described by referring to FIGS. 1-7.

In one embodiment of the present invention. FIG. 1 shows a multi-layered safety spectacles 100 used for this invention comprising a one-piece, polycarbonate main lens 106 and a pair of dually adjustable-angle and adjustable-length temples 102. The pair of dually adjustable-angle and adjustable-length temples 102 is attached at the edges of the main lens as shown in FIG. 1. Four arrows indicated in FIG. 1 show adjustable movement made possible by the pair of dually adjustable-angle and adjustable-length temples 102. In one embodiment of the present invention, a pair of rubber nose pad 104 is attached near a lower-center portion of the polycarbonate main lens 106.

Figure 2B:
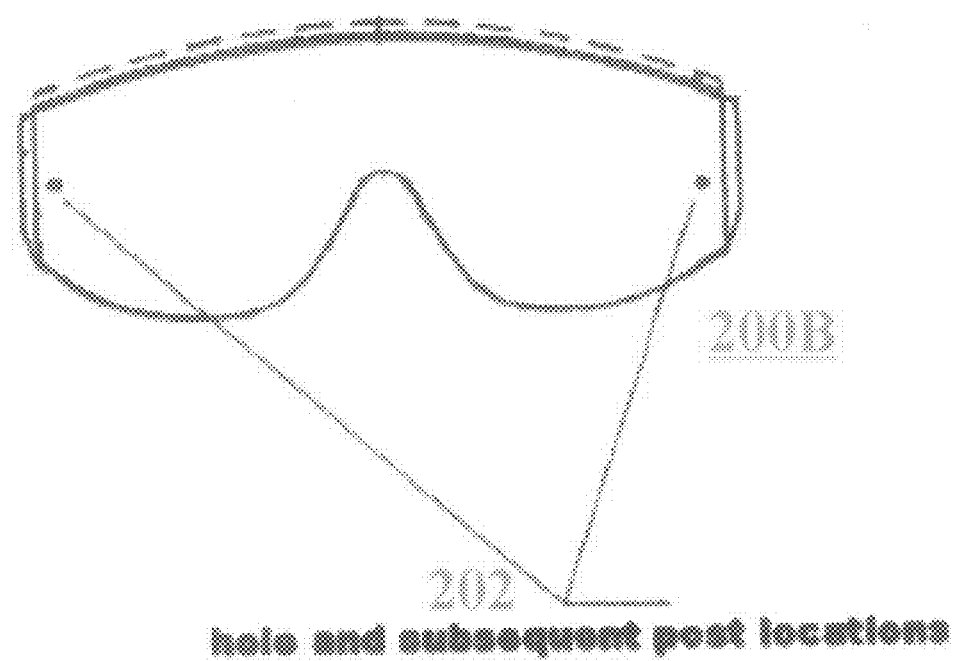
FIG. 2B shows a frontal view of a main lens on the multi-layered safety spectacles with drilled holes in the main lens, which forms subsequent post locations in accordance with an embodiment of the present invention.
Figure 3:
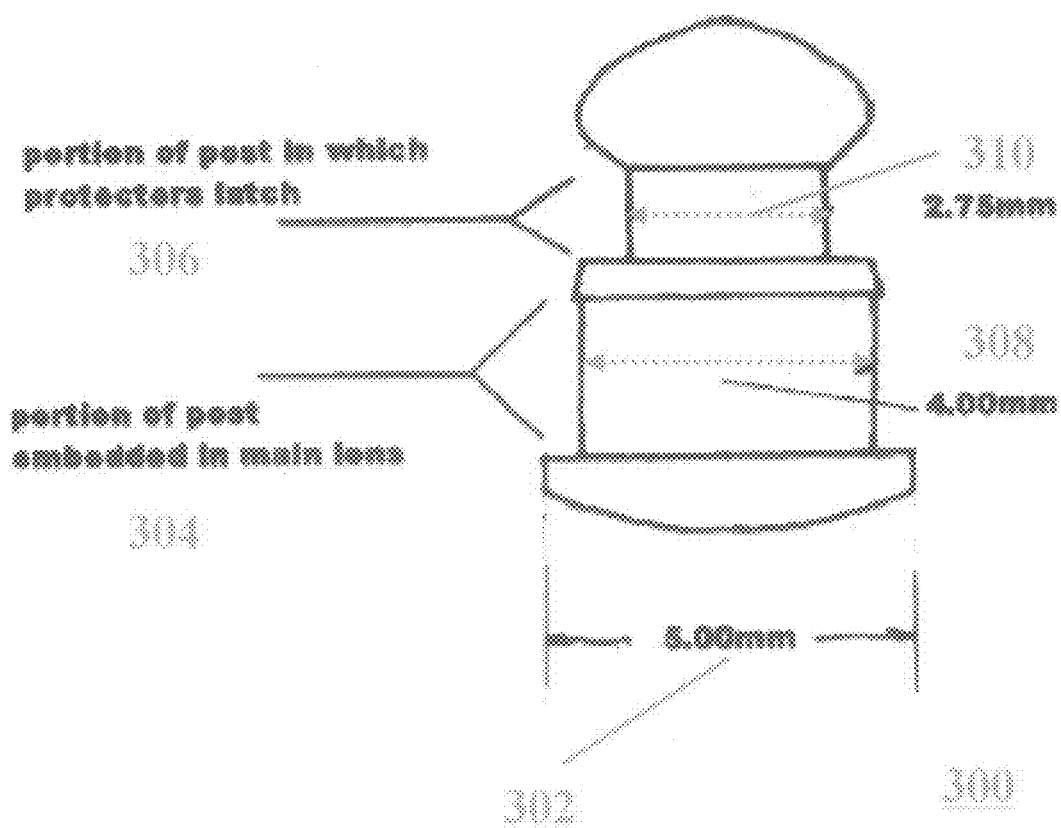
FIG. 3 shows a side view of a protruding post which is partially embedded within the drilled holes denoted in FIG 2B in accordance with an embodiment of the present invention.

FIG. 2A shows a frontal view of a main lens 200A (e.g. a polycarbonate main lens 106 from FIG. 1) before holes are drilled into the main lens 200A to place protruding posts (e.g. as shown in FIG. 3). FIG. 2B shows one embodiment of the present invention in which two holes 202 are drilled into the main lens 200B at the approximate locations noted by the holes 202 in FIG. 2B. In one embodiment of the present invention, within each hole 202 in the main lens 200B, a small, rounded, and plastic post 300, as shown in FIG. 3, will be partially embedded. An upper portion 306 of the post 300 will be allowed to protrude from the main lens and specifically act as a "protruding" post for "sliding-i" or inserting notches from a multiple number of lens protectors placed on top of the main lens. A lower portion 304 of the post 300 is typically embedded in the main lens and securely attached to the main lens. In one embodiment of the present invention, the width 310 of the upper portion 306 of the post 300 is 2.75 mm and the width 308 of the lower portion 304 of the post 300 is 4.00 mm. Embedding post 300 into the main lens provides a means of placing multiple layers of lens protectors.

Figure 4B:
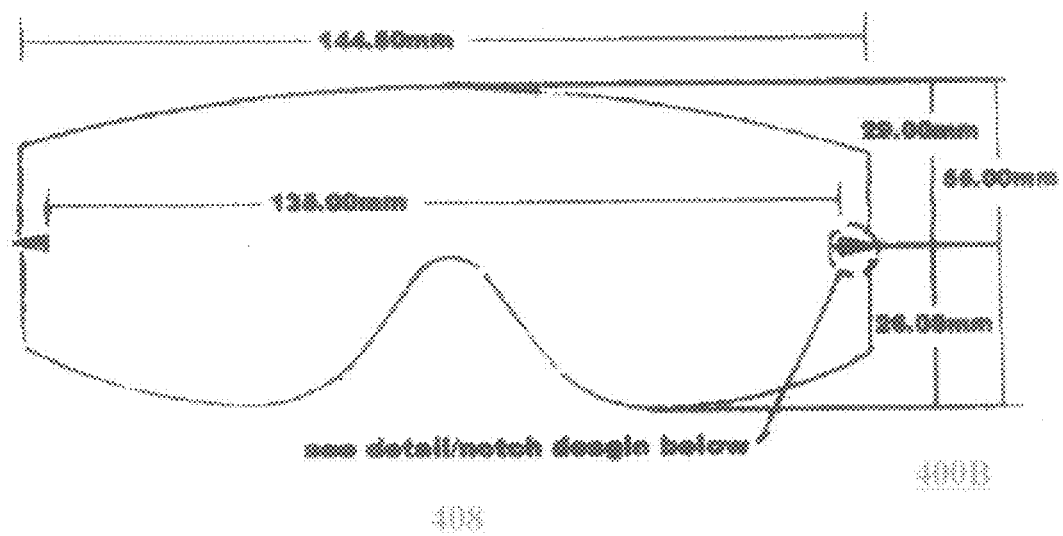
FIG. 4B shows a frontal view of the transparent lens protector configured to be placed on top of the main lens, wherein a notch design is illustrated in accordance with an embodiment of the present invention.

FIG. 4A shows one transparent lens protector 400A with uniquely-shaped notches 404 and 406 at the opposite ends of the transparent lens protector 400A. In one embodiment of the invention, a plurality of the die cut, polyester, and transparent lens protectors with 0.003-0.005" in thickness and generally the shape of the front of the main lens is securely placed in front of the main lens by sliding-in or inserting each notch (e.g. 404 and 406) of each transparent lens protector 400A to the protruding posts (e.g. 608 of FIG. 6) The corresponding specific details of the notch design is shown in FIGS. 4B and 5. FIG. 4B is an embodiment of the present invention with examples of dimensions used for producing a transparent lens protector 400B. It is important to note that one of the unique features of the present invention is the shape, design and functions of a notch 408 because the notch 408 enables a "pinch-off" removal of the transparent lens protector 400B from the main lens without requiring tabs or any other pulling devices. The notch 408 of FIG. 4B is illustrated in more detail in FIG. 5 with a zoomed-in view of the notch 500. In one embodiment of the invention, the notch 500 has a larger height (e.g. 3.0 mm) in an inner sidewall 504 of the notch (i.e. closer to a nose pad portion of the main lens) than in an outer-edge sidewall-less opening (e.g. 1.5 mm) 508 of the notch. This difference in height for the notch 500 enables a protruding post (e.g. FIG 3.) to latch the notch tightly in the upper portion of the protruding post (e.g. 306 of FIG. 3). Furthermore, an outer-edge sidewall-less opening 508 in the design of the notch 500 enables a user to remove one layer of transparent lens protector by using a pinching motion on the surface of the transparent lens protector to slide off a layer of transparent lens protector through a notch space 506, without resorting to pulling a tab or a tear-off grip. It is important to note that the design of the notch 500 specifically enables the pinching motion from the user and is unique to the present invention for multi-layer safety spectacles. The design and shape of the notch 500 serve as a clear distinguisher between the present invention and any prior art.

Figure 6:
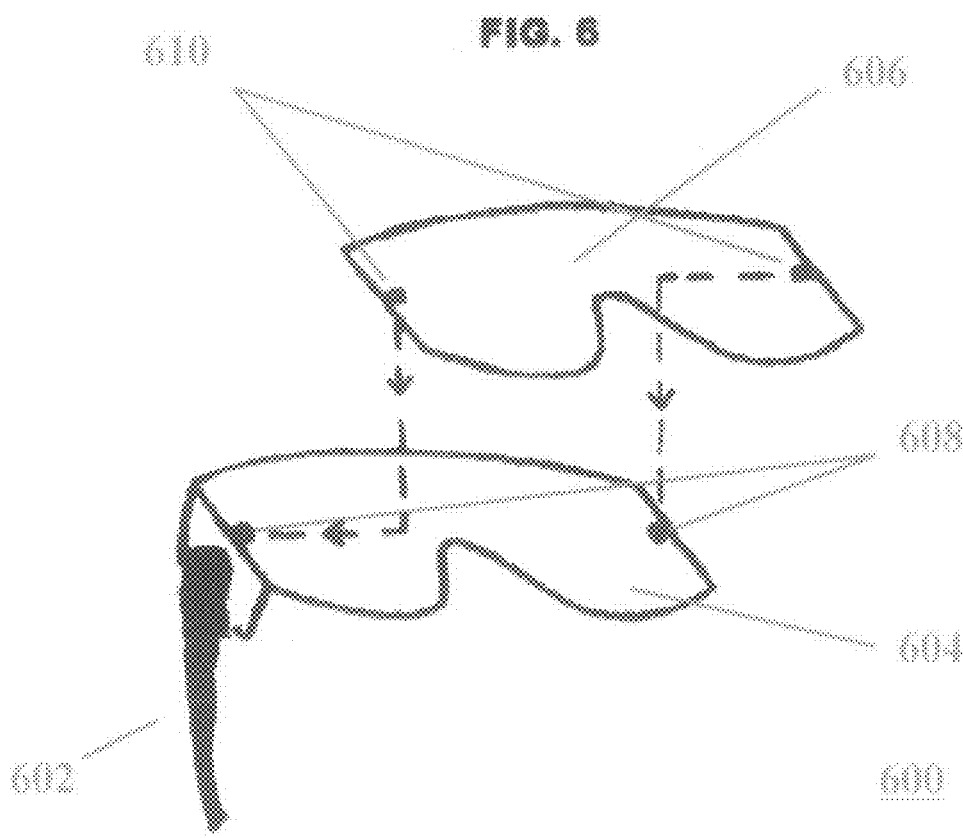
FIG. 6 shows a perspective view of the process of attaching lens protectors to the main lens of safety glasses in accordance with an embodiment of the present invention.
Figure 7:
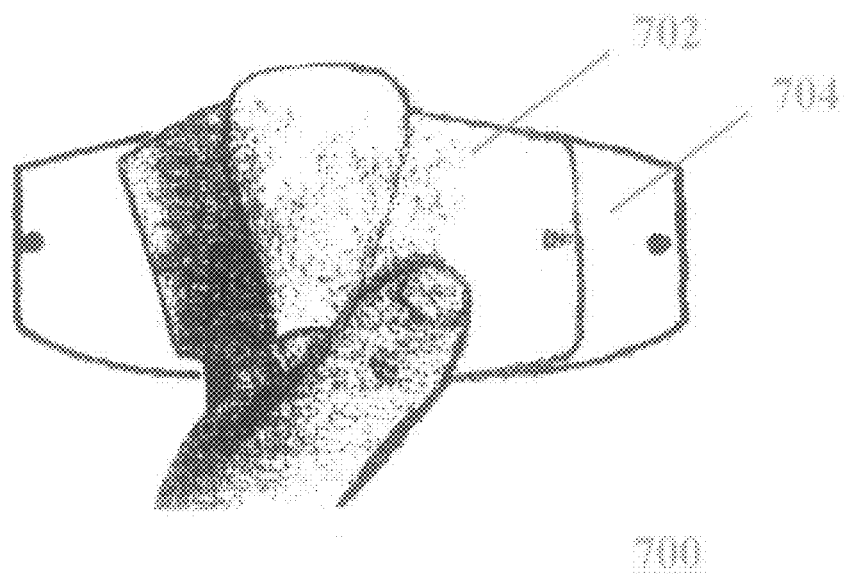
FIG. 7 shows a frontal view of the process for removing the outermost protector using a pinching motion in accordance with an embodiment of the present invention.

FIG. 6 shows an illustration of placing a transparent lens protector 606 on top of a main lens 604 of multi-layer safety spectacles 600 by latching a pair of notches 610 onto a pair of protruding posts 608, in accordance with an embodiment of the present invention. As shown in FIG. 5 by an outer-edge sidewall-less opening 508, each side edge of the notch 610 has an outer-edge sidewall-less opening and therefore enables a pinch motion on the surface of the transparent lens protector 606 to remove a layer of transparent lens. The shape and design of the pair of notches 610 in accordance with the present invention are clearly a non-obvious and distinguishing feature from conventional multi-layer safety spectacles, which use holes instead of notches to latch each transparent lens protector layer, thereby necessitating the use of pulling tabs or tear-off grips.

FIG. 1 shows how to remove the outermost transparent protector 702 as the user becomes subject to constant fallout of debris, general exposure to light-weight paint particles, chemicals, or other debris. The present invention for multi-layer safety spectacles enable continuous eye protection by simply "pinching-off" the outermost protector 702 to reveal a new layer of lens protector 704, as shown in FIG. 1, as the outermost protector 702 becomes soiled or covered with paint or chemicals. This simple pinching motion is enabled by the unique design of the pair of notches on the side edges of each lens protector, which allows the side edges of the lens protectors to simply slide off or de-latch from protruding posts on the main lens. The pinching motion on the surface of the outermost protector 702 typically exposes another clean lens protector, ready to function in the same manner.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. An improved apparatus for multi-layered safety spectacles, the improved apparatus comprising:

a transparent main lens portion configured to cover an area surrounding a user's eyes to protect the user's eyes from debris, paint particles, or chemicals;

a pair of temples attached to edges of a rear surface of the transparent main lens portion;

a protruding post partially embedded in the transparent main lens portion, wherein the protruding post comprises a lower portion embedded in the main lens portion and an upper portion protruding above a front surface of the transparent main lens portion; and a transparent lens protector with a notch on each side edge of the transparent lens protector, wherein the notch is configured to latch onto the upper portion of the protruding post and wherein a height of the notch is larger in an inner sidewall than in an outer-edge sidewall-less opening configured to slide-off the transparent lens protector from the transparent main lens portion by pinching with two fingers placed near a center portion of the transparent lens protector.

2. The improved apparatus of claim 1, wherein the transparent lens protector with the notch on each side edge of the transparent lens protector is also configured to be removed from the upper portion of the protruding post by pinching a front surface of the transparent lens protector with at least two fingers placed near a center portion of the front surface.

3. The improved apparatus of claim 1, wherein the pair of temples is height and length-adjustable.

4. The improved apparatus of claim 1, further comprising a pair of nose pads attached to a lower center portion of the rear surface of the transparent main lens portion.

5. The improved apparatus of claim 1, wherein the transparent main lens portion is made of polycarbonate.

6. The improved apparatus of claim 1, wherein the transparent lens protector is made of polyester and substantially in similar shape to the front surface of the transparent lens portion.

7. The improved apparatus of claim 1, wherein the upper portion of the protruding post is configured to latch a plurality of notches from a plurality of transparent lens protectors.

8. A method for replacing an outermost transparent lens protector with a clean underlying transparent lens protector for multi-layered safety spectacles, the method comprising:
   placing at least two fingers on a front surface of the outermost transparent lens protector located above a main lens portion of the multi-layered safety spectacles, wherein the outermost transparent lens protector has a notch on each side edge of the outermost transparent lens protector and the notch is latched onto a protruding post attached to the main lens portion;
   sliding-off the notch from the protruding post attached to the main lens portion by pinching the front surface of the outermost transparent lens protector with at least two fingers placed near a center portion of the front surface, wherein a height of the notch is larger in an inner sidewall than in an outer-edge sidewall-less opening of the notch; and
   removing the outermost transparent lens protector from the main lens portion to reveal the clean underlying transparent lens protector for the multi-layered safety spectacles.

9. The method of claim 8, wherein the protruding post is partially embedded in the main lens portion and partially protruding above the front surface of the outermost transparent lens protector.

10. The method of claim 8, wherein the outermost transparent lens protector does not have tabs, tear-off grips, or any other pulling devices.

11. The method of claim 8, wherein the outermost transparent lens protector is made of polyester and substantially in similar shape to a front surface of the main lens portion.

12. A pinch-off multi-layer lens protection system for safety glasses, the pinch-off multi-layer lens protection system comprising:
   a transparent main lens portion configured to cover an area surrounding a user's eyes to protect the user's eyes from debris, paint particles, or chemicals;
   a pair of temples attached to edges of a rear surface of the transparent main lens portion;
   a protruding post partially embedded in the transparent main lens portion, wherein the protruding post comprises a lower portion embedded in the main lens portion and an upper portion protruding above a front surface of the transparent main lens portion; and
   a transparent lens protector with a notch on each side edge of the transparent lens protector, wherein a height of the notch is larger in an inner sidewall than in an outer-edge sidewall-less opening and wherein the notch is configured to latch onto the upper portion of the protruding post protruding above the front surface of the transparent main lens portion.

13. The pinch-off multi-layer lens protection system of claim 12, further comprising a pair of nose pads attached to a lower-center portion of the rear surface of the transparent main lens portion.

14. The pinch-off multi-layer lens protection system of claim 12, wherein the transparent lens protector with the notch on each side edge of the transparent lens protector is also configured to be removed from the upper portion of the protruding post by pinching a front surface of the transparent lens protector with at least two fingers placed near a center portion of the front surface.

15. The pinch-off multi-layer lens protection system of claim 12, wherein the pair of temples is height and length-adjustable.

16. The pinch-off multi-layer lens protection system of claim 13, wherein the pair of nose pads are made of rubber.

17. The pinch-off multi-layer lens protection system of claim 12, wherein the transparent main lens portion is made of polycarbonate.

18. The pinch-off multi-layer lens protection system of claim 12, wherein the transparent lens protector is made of polyester and substantially in similar shape to the front surface of the transparent lens portion.

19. The pinch-off multi-layer lens protection system of claim 12, wherein the upper portion of the protruding post is configured to latch a plurality of notches from a plurality of transparent lens protectors.

* * * * *